United States Patent [19]

Hoffman et al.

[11] Patent Number: 5,223,437
[45] Date of Patent: Jun. 29, 1993

[54] DIRECT FIBRINOGEN ASSAY

[75] Inventors: Julie F. Hoffman, Ann Arbor, Mich.; Janet B. Callahan, Carrboro; C. Hermas Swope, Raleigh, both of N.C.

[73] Assignee: Akzo N.V., Arnhem, Netherlands

[21] Appl. No.: 696,569

[22] Filed: May 8, 1991

Related U.S. Application Data

[63] Continuation of Ser. No. 443,948, Dec. 1, 1989, abandoned.

[51] Int. Cl.⁵ .................. G01N 21/00; G01N 21/75
[52] U.S. Cl. .................. 436/164; 422/82.09; 435/13
[58] Field of Search ............ 422/73, 58, 82.05, 82.09; 436/8–18, 164; 435/13

[56] References Cited

U.S. PATENT DOCUMENTS 3,658,480  4/1972  Kane et al. .
3,833,864  9/1974  Kiess et al. .
3,861,877  1/1975  Matharani et al. .
3,989,382  11/1976  Kent et al. .
4,659,550  4/1987  Schildknecht .................. 422/73
4,720,787  1/1988  Lipscomb .................. 422/73

OTHER PUBLICATIONS

Brown, *Hematology:, Principles and Procedures*, Third Edition, 1982 by Lea & Febiger, Pa., pp. 15–16.
Henry et al., *Clinical Chemistry, Principles and Technics, Bio-Science Laboratory*, Second Edition, 1974 by Harper and Row, N.Y., pp. 453–455–460.

*Primary Examiner*—James C. Housel
*Assistant Examiner*—N. Bhat
*Attorney, Agent, or Firm*—Spencer, Frank & Schneider

[57] ABSTRACT

An endpoint assay for measuring fibrinogen utilizing strong thrombin and weak plasma. In a preferred embodiment the assay is based on the direct conversion of a normalized signal from a sensor to fibrinogen concentration.

5 Claims, No Drawings

DIRECT FIBRINOGEN ASSAY

CROSS-REFERENCE TO RELATED APPLICATION

This application is a continuation application of application No. 07/443,948 filed Dec. 1, 1989, and now abandoned.

BACKGROUND OF THE INVENTION

The invention relates to a method for determining the concentration of fibrinogen in blood plasma using thrombin as a reagent.

Prior methods of using thrombin to measure fibrinogen concentration, include the Clauss method which is based on measuring the time it takes for a plasma-thrombin reaction to occur (clotting time) and the ACL3 fibrinogen assay. The Clauss method is described in *Manual of Hemostasis and Thrombosis*, ed. 3, by Arthur R. Thompson and Laurence A. Harker, Appendix A, p. 179 (1983) and in *Gerrinnungs physiologische schnell Methode zur Bestimmung des Fibrinogens* by A. Clauss, Acta Haematol, 17:237 (1957). The ACL3 method is described in *Method for the Determination of Functional (Clottable) Fibrinogen by the New Family of ACL Coagulometers* by E. Rossi, P. Mondonico, A. Lomabardi, L. Preda, Thrombosis Research 52; 453–469 (1988). These methods rely on the measurement of a relevant parameter such as clotting time or changes in optical transmission and on multiple dilutions of a calibrator plasma to compensate conditions of the instrument and reagent at a given time. Using calibrator plasmas (i.e. plasma having known fibrinogen concentrations) "standard lines" or "calibration curves" must be constructed repeatedly whenever conditions warrant. In the determination of fibrinogen concentration of an unknown sample, the relevant quantity, such as clotting time, is measured and the concentration is then "read" from the standard curve. This process can involve considerable calculation, and is often tedious and time consuming.

Another deficiency of these prior methods is that the relevant quantity being measured is often instrument dependent, as well as reaction dependent. For example, if the instrument used to measure the relevant parameter employs an electro-optical system in which scattered or transmitted light is detected, the value obtained from the measurement will depend on the signal level measured by the optical sensor, which in turn depends on the amount of light incident on the reaction vessel as well as the electronic gains used in association with the optical sensor. The values of these quantities do not remain constant in time, nor do they remain constant from channel to channel or instrument to instrument.

SUMMARY OF THE INVENTION

Therefore, it is an object of the invention to provide a method for measuring the concentration of fibrinogen in a blood sample that is more efficient and efficacious [manner] than prior methods.

It is another object of the invention to eliminate the effects of instrument variation and channel variation in measuring the changes in optical transmission, which are the basis for determining fibrinogen concentration.

It is also an object of the invention to employ measured quantities in a manner that eliminates the need to repeatedly establish a standard curve.

The present invention provides a method for measuring the concentration of fibrinogen in a blood plasma sample. According to the method of the invention, a sample of plasma containing fibrinogen is provided in a container. Thrombin is added to the sample and mixed with the sample to form a reaction mixture. An initial optical transmittance is measured for the reaction mixture. The thrombin and fibrinogen are allowed to react with each other in the reaction mixture. A final optical transmittance is measured for the reaction mixture. The measurements are manipulated in the manner described below and concentration of fibrinogen is determined from a previously established standard curve.

It is an aspect of the invention that the standard curve is constructed in such a manner that it remains unchanged by variations in instrument, reagent or sample. Therefore, once established, it is not necessary to repeatedly reconstruct it.

DESCRIPTION OF THE PREFERRED EMBODIMENTS

The present method is preferably used in conjunction with an optical monitoring system such as that disclosed in concurrently filed U.S. Pat. No. 5,002,392 issued Mar. 26, 1991 to Swope et al., entitled "Multichannel Optical Monitoring System", assigned to the assignee of the present application, the disclosure of which is incorporated herein by reference, or in conjunction with commercially available hemostasis instruments such as the assignee's model Coag-A-Mate XC or model Coag-A-Mate XM.

Approximate reagent/plasma concentrations that are suitable for the method of the invention are known from the Clauss fibrinogen method noted above. The thrombin concentration is preferably about 100 NIH units (a strong thrombin concentration) and the plasma sample is preferably diluted in a 1:10 ratio (a weak plasma concentration) with Owren's Veronal Buffer (sodium barbital). Other suitable diluents for the plasma are described in Clauss.

In the present invention the formation of fibrinogen is photo-optically monitored for total change between the optical transmittance before the onset of the reaction and the optical transmittance at the conclusion of the reaction. According to the method, reagent is added to plasma and, after a time which allows for complete sample-reagent mixing, an initial transmittance signal ($T_i$) is recorded. When the clot is fully formed, the final transmittance signal ($T_f$) is processed as described below.

The relevant parameter, delta or D, is computed the initial and final transmittance measurements by normalizing the difference in the readings to the initial value plus any offset using the following equation:

$$D = \frac{T_i - T_f}{T_i + S_0} \times K$$

where

D is the normalized digital value of delta;

$T_i$ is the digital value of the transmitted light prior to the onset of the clot;

$T_f$ is the digital value of the transmitted light subsequent to the formation of the clot;

$S_0$ is the digital offset that may have been imposed as part of the instrument design; and K is an arbitrary constant chosen for convenience.

It should be noted that in prior methods, D was defined as the difference ($T_i - T_f$) only. The denominator in the above expression represents the normalization of D to the initial value of the transmittance.

The next step in determining the concentration of fibrinogen of an unknown sample is to refer the above determined value of D to the concentration by the use of a standard curve. This is done by first computing the quantity $$R = \log\left(\frac{D}{D_c}\right)$$

where $D_c$ is the previously determined delta for a calibrator plasma of known fibrinogen concentration.

Measurements of $D_c$ are performed relatively infrequently as changes in test conditions warrant. The next step is to use a previously determined correlation equation which describes the relationship between R and fibrinogen concentration to determine the fibrinogen concentration of the sample. It has been discovered that the correlation equation relating R and fibrinogen concentration does not change significantly with different designated reagents and calibrator plasmas. Therefore, it can be permanently stored as part of the computational software and does not require periodic recomputation.

The correlation equation is preferably derived as follows: Various standard plasmas of known fibrinogen concentration are prepared and a delta value $D_s$ is determined for each standard plasma. Next, a value $R_s$ is calculated for each standard plasma based on the following equation:

$$R_s = \log\left(\frac{D_s}{D_c}\right)$$

where $R_s$ is the R value for a standard plasma;

$D_s$ is the measured delta value for the standard plasma; and $D_c$ is the previously determined delta for the calibrator plasma.

The correlation equation is then derived by plotting $R_s$ versus $\log(C_s/C_c)$ for the various standard plasmas where $C_s$ is the fibrinogen concentration of a standard plasma and $C_c$ is the fibrinogen concentration of the calibrator plasma.

It will be understood that the above description of the present invention is susceptible to various modifications, changes and adaptations, and the same are intended to be comprehended within the meaning and range of equivalents of the appended claims.

What is claimed is:

1. A method for optically measuring a concentration of fibrinogen in a blood plasma sample, said method comprising:

providing a sample of plasma containing fibrinogen in a container;

adding thrombin to the sample;

mixing the thrombin with the sample to form a reaction mixture;

measuring an initial optical transmittance for the reaction mixture;

allowing the thrombin and fibrinogen to react with each other in the reaction mixture;

measuring a final optical transmittance for the reaction mixture;

comparing the final transmittance measurement to the initial transmittance measurement to compute a delta value; and determining the concentration of fibrinogen based on the delta value 2. The method of claim 1, wherein the thrombin is at a concentration of about 100 NIH units and the plasma sample is diluted in about a 1:10 ratio with sodium barbital.

3. The method of claim 1, wherein the delta value is computed according to the equation:

$$D = \frac{T_i - T_f}{T_i + S_0} \times K$$

where

D is a normalized value of delta;

$T_i$ is the initial optical transmittance of the sample;

$T_f$ is the final optical transmittance of the sample;

$S_0$ is an offset which is dependent on the device used to perform said method; and K is a predetermined constant.

4. The method of claim 3, wherein said step of determining fibrinogen concentration further comprises:

deriving a correlation equation which allows fibrinogen concentration of a sample to be determined from a value R, where R is computed from the equation $$R = \log\left(\frac{D}{D_c}\right)$$

where

D is the delta value of the sample plasma; and $D_c$ is a delta value of a calibrator plasma; and determining the fibrinogen concentration of the plasma sample based on the derived correlation equation.

5. The method of claim 4, wherein the correlation equation is derived by:

measuring a delta value for a plurality of standard plasmas of different known concentrations;

measuring a delta value for a calibrator plasma of known concentration;

and plotting $R_s$ versus the $\log(C_s/C_c)$ for the plurality of standard plasmas where $$R_s = \log\left(\frac{D_s}{D_c}\right)$$

where $R_s$ is the R value for a standard plasma;

$D_s$ is a measured delta value for the standard plasma;

$D_c$ is a measured delta value for a calibrator plasma;

$C_s$ is the concentration of fibrinogen in the standard plasma; and $C_c$ is the concentration of fibrinogen in the calibrator plasma.

* * * * *